(12) United States Patent
Wang

(10) Patent No.: US 9,946,243 B2
(45) Date of Patent: Apr. 17, 2018

(54) EEFIT-BASED ELECTROMAGNETIC WAVE ENERGY CONDUCTING EQUIPMENT

(71) Applicant: Nick Wang Technology Limited, Hong Kong (CN)

(72) Inventor: Nan Wang, Hong Kong (CN)

(73) Assignee: NICK WANG TECHNOLOGY LIMITED, Tsuen Wan, N.T. (HK)

( * ) Notice: Subject to any disclaimer, the term of this patent is extended or adjusted under 35 U.S.C. 154(b) by 0 days.

(21) Appl. No.: 15/061,476

(22) Filed: Mar. 4, 2016

(65) Prior Publication Data
US 2017/0102684 A1    Apr. 13, 2017

(30) Foreign Application Priority Data
Oct. 9, 2015    (CN) .................... 2015 2 0779650 U

(51) Int. Cl.
| | |
|---|---|
| *H05B 3/00* | (2006.01) |
| *G05B 19/05* | (2006.01) |
| *H05K 7/14* | (2006.01) |
| *A61N 5/06* | (2006.01) |

(52) U.S. Cl.
CPC ............. *G05B 19/05* (2013.01); *A61N 5/06* (2013.01); *H05K 7/1467* (2013.01); *A61N 2005/066* (2013.01)

(58) Field of Classification Search
USPC ........................................... 700/230
See application file for complete search history.

(56) References Cited

U.S. PATENT DOCUMENTS

| | | | | | |
|---|---|---|---|---|---|
| 4,228,345 | A | * | 10/1980 | Sticker | B65B 53/02 219/388 |
| 4,486,172 | A | * | 12/1984 | Dunning | B29B 13/023 219/388 |
| 2010/0220983 | A1 | * | 9/2010 | Doherty | F26B 3/283 392/411 |
| 2011/0013892 | A1 | * | 1/2011 | Ragay | H05B 3/0076 392/411 |
| 2012/0178105 | A1 | * | 7/2012 | Halloran | G01N 33/92 435/7.92 |
| 2014/0017848 | A1 | * | 1/2014 | Ragay | H05B 3/0076 438/72 |

* cited by examiner

*Primary Examiner* — Kyle O Logan
(74) *Attorney, Agent, or Firm* — Muncy, Geissler, Olds & Lowe, P.C.

(57) ABSTRACT

The utility model discloses an EEFIT-based electromagnetic wave energy conducting equipment, having an enclosure, a skeleton, main emission sources, conveying devices and a PLC. The skeleton is arranged in the enclosure, the main emission sources are arranged on the skeleton, the conveying devices are arranged beside the main emission sources, and the conveying devices are electrically connected with the PLC. Each conveying device has a conveyor belt and limit rods. Two limit rods are arranged on each conveyor belt. The limit rods are respectively driven by two independent stepping motors. The EEFIT-based electromagnetic wave energy conducting equipment has the advantages of wider application range, more functions and lower cost, can be applicable to the irradiation of common or fragile materials, and can handle the materials on the same equipment according to different references. The manufacturing and maintenance costs are lower, and the failure rate is smaller as well.

10 Claims, 10 Drawing Sheets

EEFIT-BASED ELECTROMAGNETIC WAVE ENERGY CONDUCTING EQUIPMENT

TECHNICAL FIELD

The utility model belongs to EEFIT-based electromagnetic wave energy conducting equipment, and particularly relates to EEFIT-based electromagnetic wave energy conducting equipment applicable to various products.

BACKGROUND ART

Far infrared ray is close to cell molecules in a human body in term of vibration frequency; after coming in a human body, the far infrared ray will promote temperature rise in a subcutaneous deep layer to expand capillaries and accelerate blood circulation, which is beneficial to removing vascular deposits and harmful substances out of the body, clearing obstacles hindering metabolism, reviving tissues again and promoting the generation of enzymes, so as to achieve the purposes of activating tissue cells, preventing aging and enhancing the immune system, and the far infrared ray has the function of ameliorating and preventing a variety of diseases caused by blood circulation and microcirculation disturbances.

Although the far infrared ray is a ray in the sunlight, capable of penetrating deepest into skin and subcutaneous tissues, the depth of the far infrared ray penetrating in the human body from outside is limited after all, how to enable the far infrared ray energy to enter human tissues more deeply, even make the far infrared ray influence various tissues and organs of the human body from inside to outside to improve various functions of the human body is a main research direction of the applicant.

To solve this problem, the applicant filed a utility model application named "Energy Molecular Water Equipment" with an Application No. 201420535730.7 on Sep. 17, 2014; in subsequent researches, the applicant found that the structure of an indexing device in the foregoing patent is relatively complex, its manufacturing cost and the subsequent maintenance cost are higher, the structure of a material output device also limits applicable products, specifically, dropping onto an output conveyor belt during output is a fatal defect for some fragile or crumbly products, and in addition, it is very inconvenient for automatic production if charging and discharging are carried out on the same side.

SUMMARY OF THE INVENTION

To solve the above problem, the utility model provides EEFIT-based electromagnetic wave energy conducting equipment, which has a more scientific structure and a wider application range.

To achieve the above purpose, the utility model adopts the following solution:

An EEFIT-based electromagnetic wave energy conducting equipment comprises an enclosure, a skeleton, main emission sources, conveying devices and a PLC; and the skeleton is arranged in the enclosure, the main emission sources are arranged on the skeleton, the conveying devices are arranged beside the main emission sources, and the conveying device is electrically connected with the PLC. Each conveying device comprises a conveyor belt and limit rods; and two limit rods are arranged on each conveyor belt, and the limit rods are respectively driven by two independent stepping motors; and the two limit rods can act like extending out or retracting back under the action of the motors to allow articles to pass or prevent articles from passing, so that the articles entering an irradiation area can be fully irradiated and other articles not entering the irradiation area are not influenced by the irradiation.

The EEFIT-based electromagnetic wave energy conducting equipment using this scheme changes the original product structure that materials are in and out from the same side, so that the material can be charged from one side and discharged from the other side, thus, the defect that materials are prone to be mixed easily when materials are in and out from the same side can be avoided; at the same time, the change of the conveyor belt structure avoids the falling action of materials happening when materials are output in the foregoing patent, and therefore the equipment can be applied to the handling of fragile materials, so that it can be adapted for energy induction of various products. For some materials that have special requirements, the conveyor belts can be stopped immediately after materials are transported out of the machine body, and then materials can be taken manually; automatic material receiving and packaging system can be arranged at the back end of the equipment for material side with no special requirements. In addition, each conveyor belt of the equipment according to this scheme can be independently operated, and each equipment can also contain a number of conveyor belts; therefore, the same equipment can deal with the same or different materials according to different conditions, which can greatly improve the practicality of the equipment. Compared with the previous indexing device, the conveying device of the scheme is simpler in structure and lower in the manufacture and maintenance cost and has lower failure rate when used normally.

Preferably, each conveying device further includes a fixed guardrail A and a movable guardrail B, one side of the movable guardrail B is provided with a second stepping motor, which drives the movable guardrail B. Guardrails are arranged on both sides of each conveyor belt to play a role in guiding materials, thus ensuring a better conveying effect of the conveyor belt; at the same time, the movable guardrail B can be used for adjusting the working size of the conveyor belt in an irradiation area according to the size of the material to improve the conveying effect.

Preferably, each conveying device further comprises an infrared induction counter; the infrared induction counter is electrically connected with the PLC and arranged directly above a first stepping motor. The infrared induction counter can calculate the quantity of materials passing, so that the PLC can set the quantity of materials irradiated each time according to the size of the irradiation area and material size and also can set the quantity of materials through the limit rods.

Preferably, the enclosure is also provided with time displays and/or LED process lamps, the time displays and the LED process lamps are respectively electrically connected with the PLC. The time displays can visually display the remaining time of the irradiation, LED progress lamps can visually display the percentage of completion of the irradiation process.

Preferably, the EEFIT-based electromagnetic wave energy conducting equipment further comprises an auxiliary emission source device. The auxiliary emission source device is composed of a base, a rail mounting plate, drawers, a driving device and auxiliary emission source blocks. The rail mounting plate is fixed on the base, the drawers can be movably matched with the rail mounting plate, and the auxiliary emission source blocks are arranged in the drawers, and the driving device is used for driving the drawers to move along the rail mounting plate. The auxiliary emission source device can emit far infrared electromagnetic wave, so as to form a protective energy field to the irradiated object and prevent the irradiated object from being interfered by energy fields of other electromagnetic waves when it is irradiated, to ensure the stability of the energy conducting process.

Preferably, the height of each infrared induction counter is adjustable. With the height-adjustable infrared induction counters, the equipment has a wider application scope and can be able to automatically handle materials with different heights; at the same time, it plays a better effect together with the movable guardrails.

Further, each main emission source is mainly composed of far infrared ceramic. Each main emission source is a single piece of far infrared ceramic material or a main emission source box provided with multiple small far infrared ceramic blocks therein. The far infrared ceramic is composed of the following raw materials in parts by weight: 40 parts of aplite, 20 parts of anorthite, 8 parts of jadeite, 15 parts of tephra, 1 part of talc, 5 parts of rhaetizite, 2 parts of platinum and 100 parts of industrial putty. The method for preparation of the far infrared ceramic comprises the following steps: grinding and abrading 2 kg of anorthite, 1.5 kg of tephra and 0.5 kg of rhaetizite, then, burning at high temperature and quickly cooling; and finally fixing and modeling together with 0.8 kg of jadeite, 4 kg of aplite, 0.1 kg of talc and 0.2 kg of platinum by use of 10 kg of industrial putty, so as to obtain 20 kg of far infrared ceramic.

Further, the fixed guardrail A and the movable guardrail B each have a wider middle part than the two ends thereof, and the two ends of the fixed guardrail A and the movable guardrail B are next to shells on two sides of the enclosure. The two ends of each guardrail are next to the shells and provided with guide devices, which can bring a better guide effect to materials.

Further, the upper portion of the enclosure is narrower than the lower portion, a front worktable and a back worktable are arranged at the front and rear sides of the enclosure, the two ends of each conveyor belt are arranged on the front worktable and the back worktable, and conveyor belt end covers are arranged on the two sides of each conveyor belt. The front and back worktables are designed to facilitate charging and discharging of the materials, especially in case of processing the materials that can only be charged and discharged manually due to special requirements. The conveyor belt end covers can play a guiding role, resulting in better conveyance effect of the conveyor belts and also avoiding the occurrence of abnormal situations where the materials are blocked by the shells.

Further, the top cover at the upper portion of the enclosure is an openable structure. The openable top cover is convenient for maintenance of the equipment.

The EEFIT-based electromagnetic wave energy conducting equipment of the utility model has the advantages of wider application range, more functions and lower cost; the EEFIT-based electromagnetic wave energy conducting equipment is applicable to irradiation of common or fragile materials and can also handle the materials on the same equipment according to different references; meanwhile, the manufacturing and maintenance costs are lower, and the failure rate is smaller as well.

Products produced by the EEFIT-based electromagnetic wave energy conducting equipment of the utility model contain energies of far infrared rays (especially energies of far infrared rays having wavelength of 8-14 microns), and when the products are used, the far infrared rays, due to the resonance effect, can improve the living quality of mankind by virtue of different types of products. The equipment of the utility model can be applied to various fields such as personal products, dietary application, electric appliances and furniture, industrial energy saving, pharmaceutical production and musical instruments, etc.

DETAILED DESCRIPTION OF THE INVENTION

Figure 1:
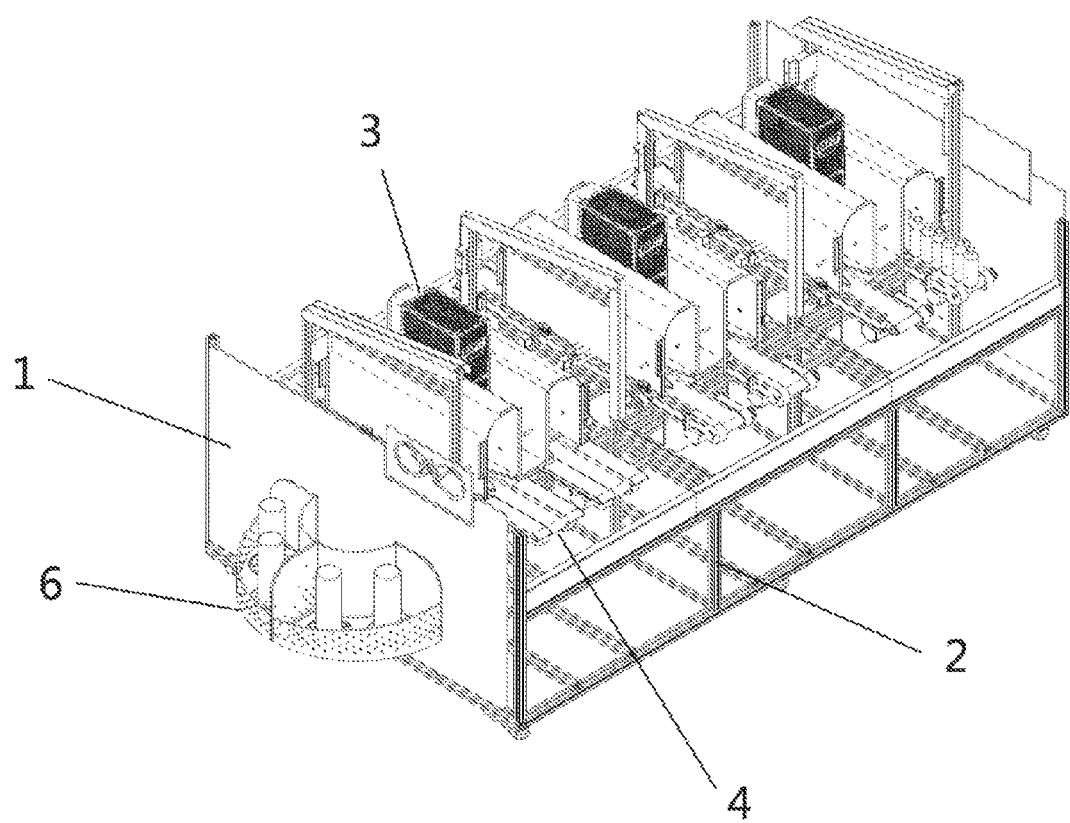
FIG. 1 is a schematic diagram of the main structure of an embodiment of the utility model.
Figure 2:
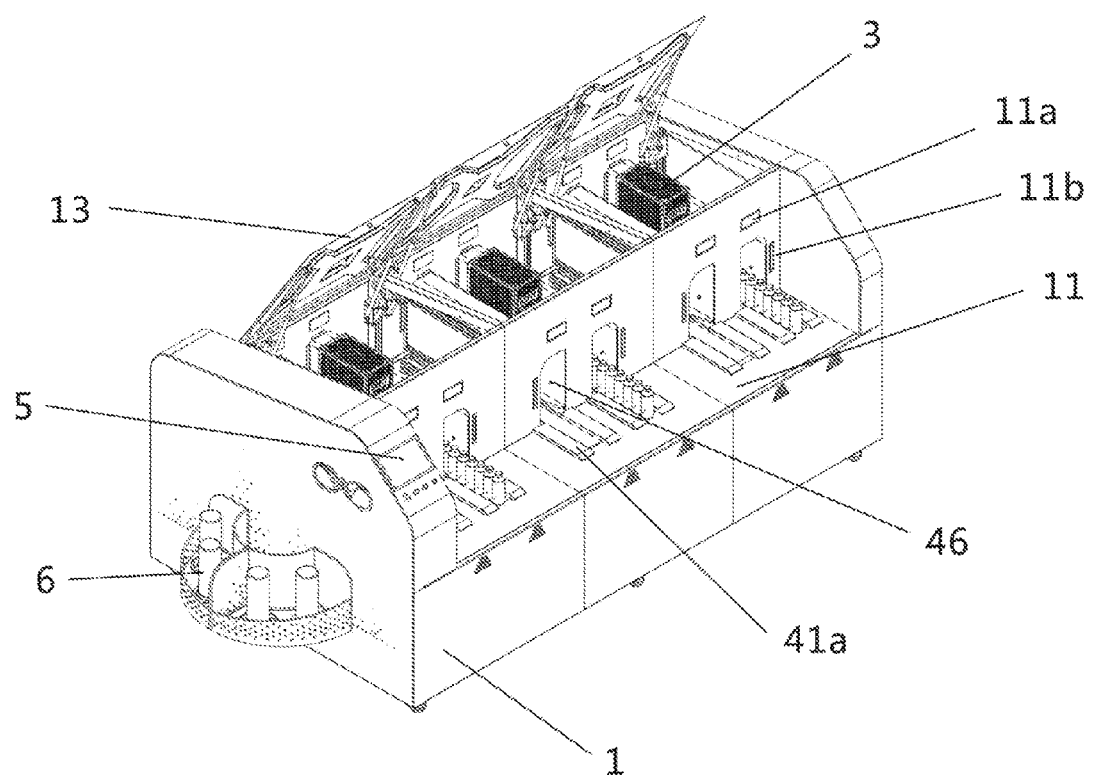
FIG. 2 is a stereoscopic front view of an embodiment of the utility model.
Figure 3:
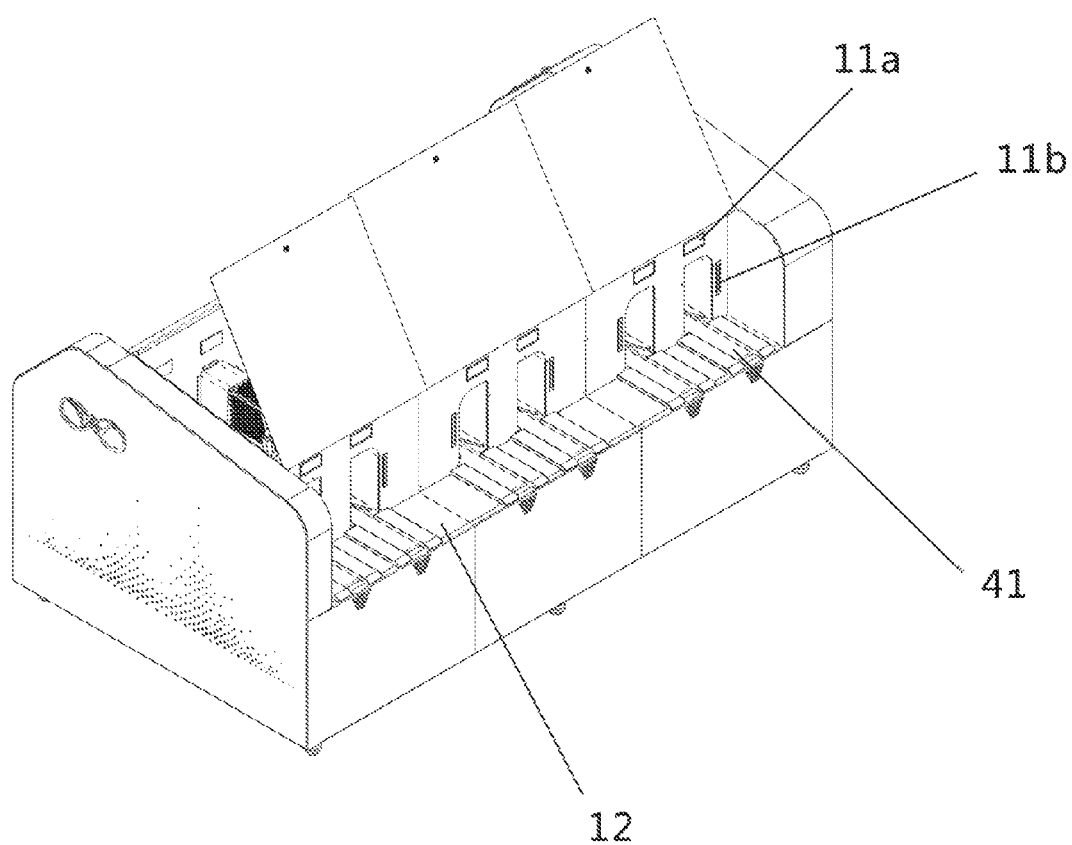
FIG. 3 is a stereoscopic rear view of an embodiment of the utility model.
Figure 4:
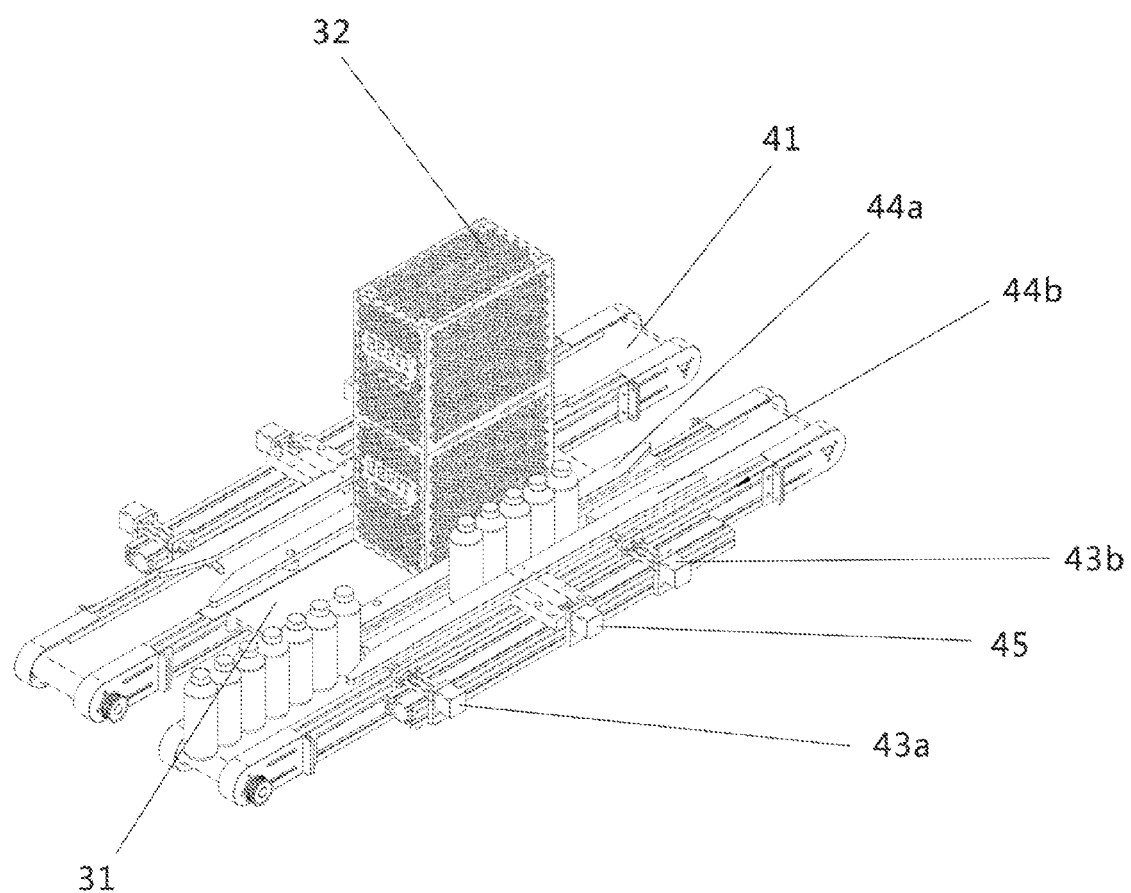
FIG. 4 is a stereoscopic schematic diagram of part of components in the embodiment of the utility model.
Figure 5:
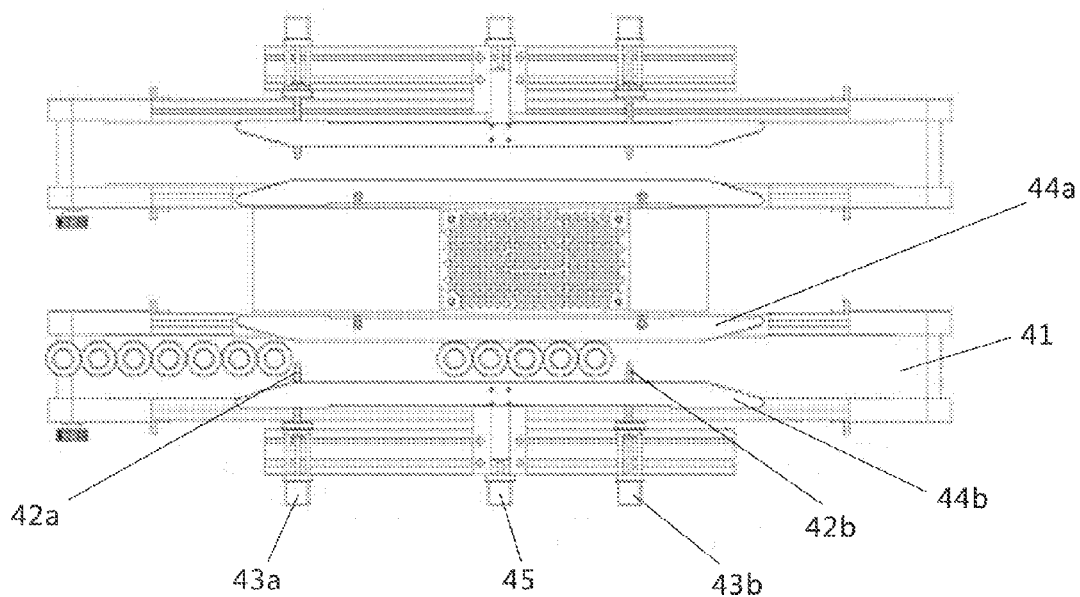
FIG. 5 is a top view of the components shown in FIG. 4.
Figure 6:
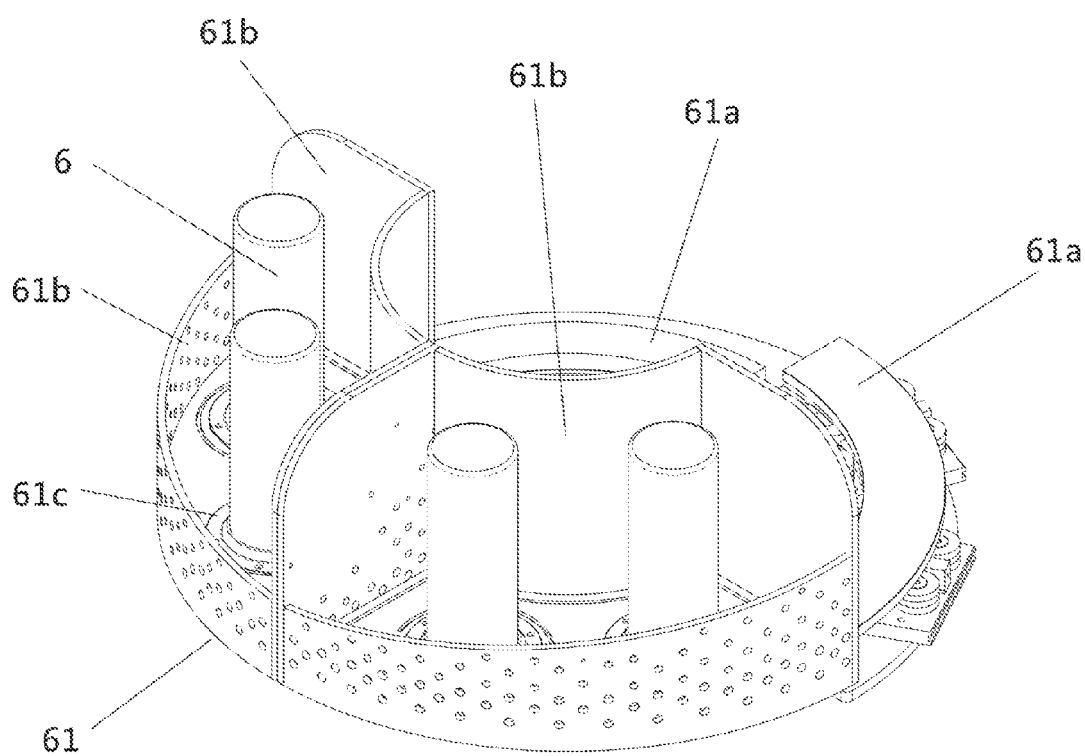
FIG. 6 is a stereoscopic schematic diagram of an auxiliary emission source holder in the embodiment of the utility model.
Figure 7:
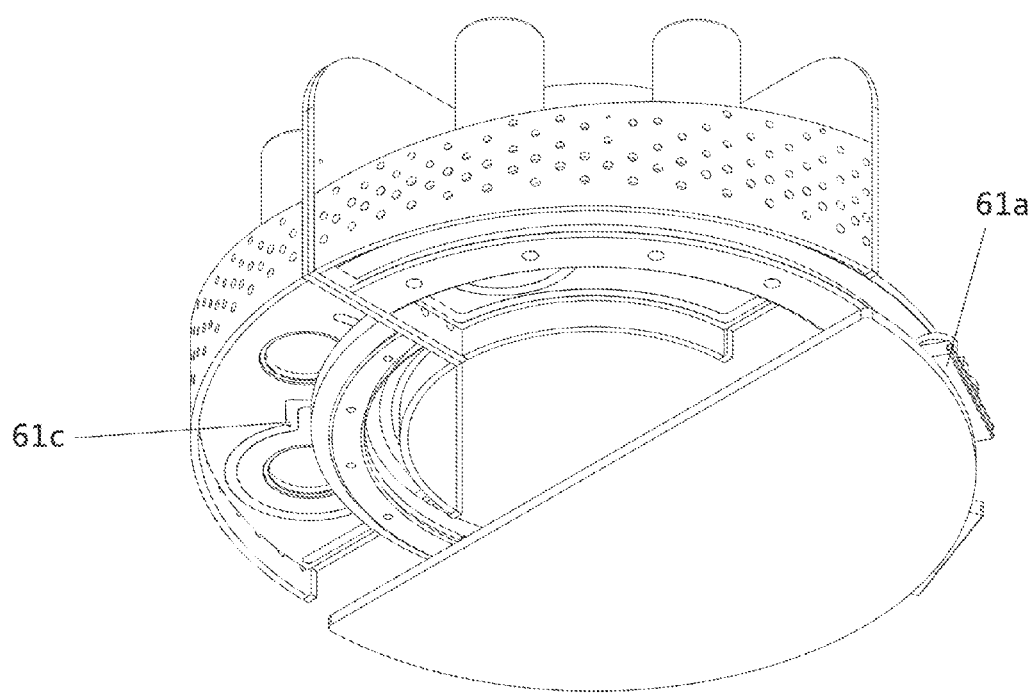
FIG. 7 is a stereoscopic bottom view of the auxiliary emission source holder shown in FIG. 6.
Figure 8:
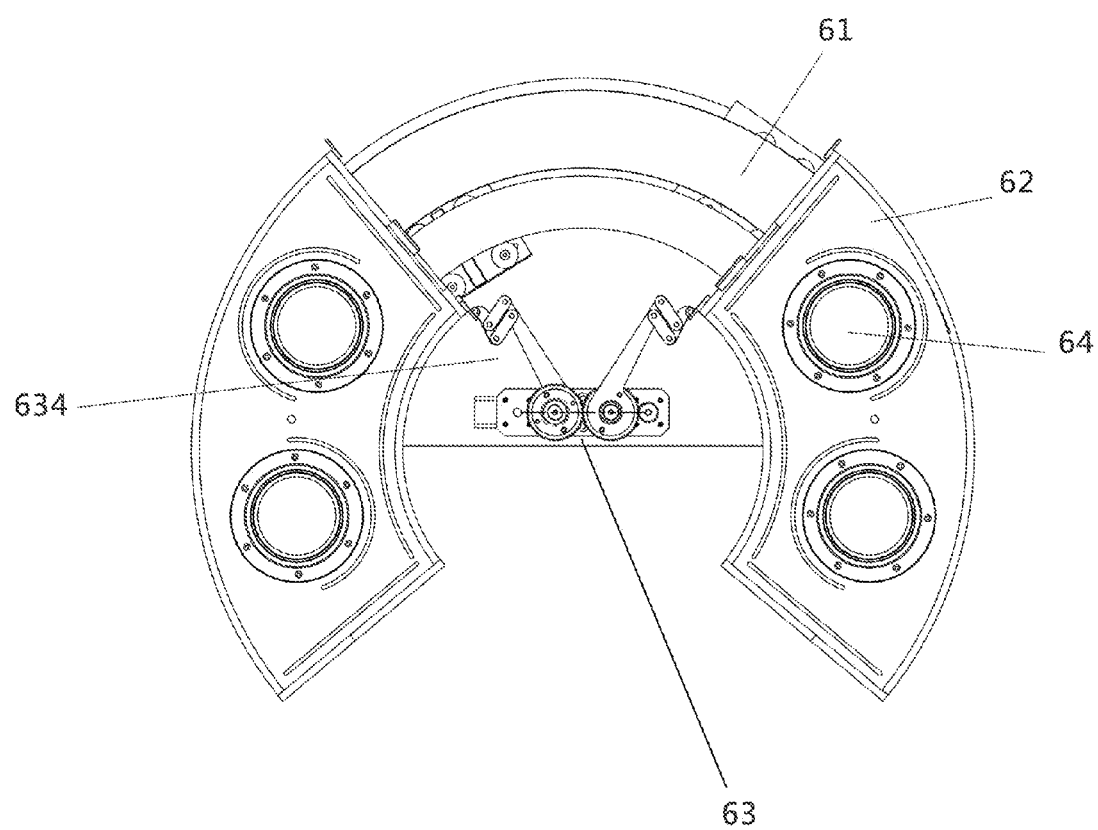
FIG. 8 is a top view of an auxiliary emission source device in a semi-open state.
Figure 9:
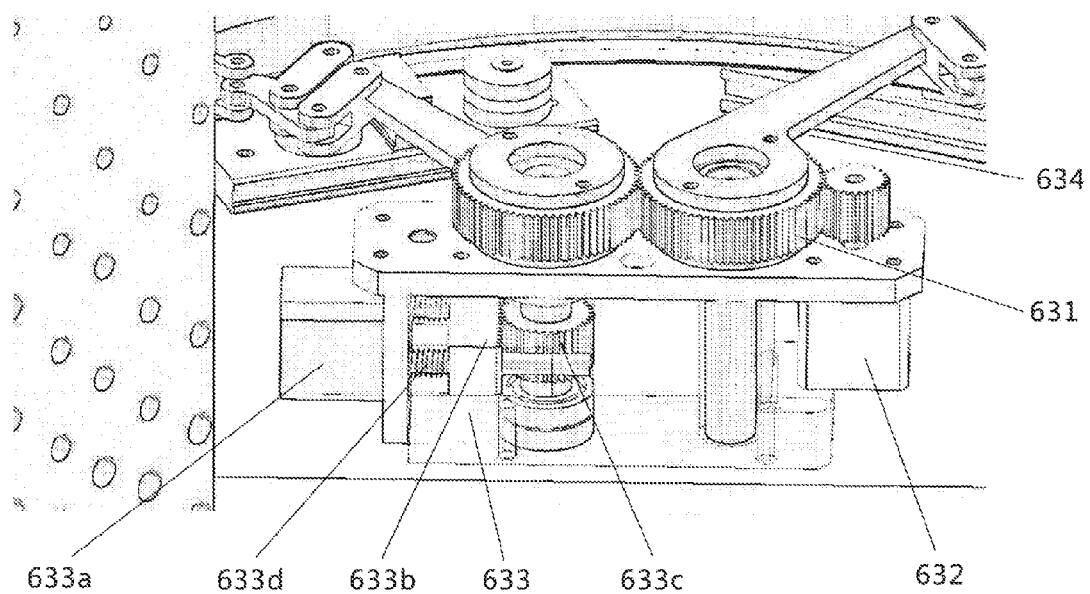
FIG. 9 is a structural schematic diagram of the driving device in a locked-up state.
Figure 10:
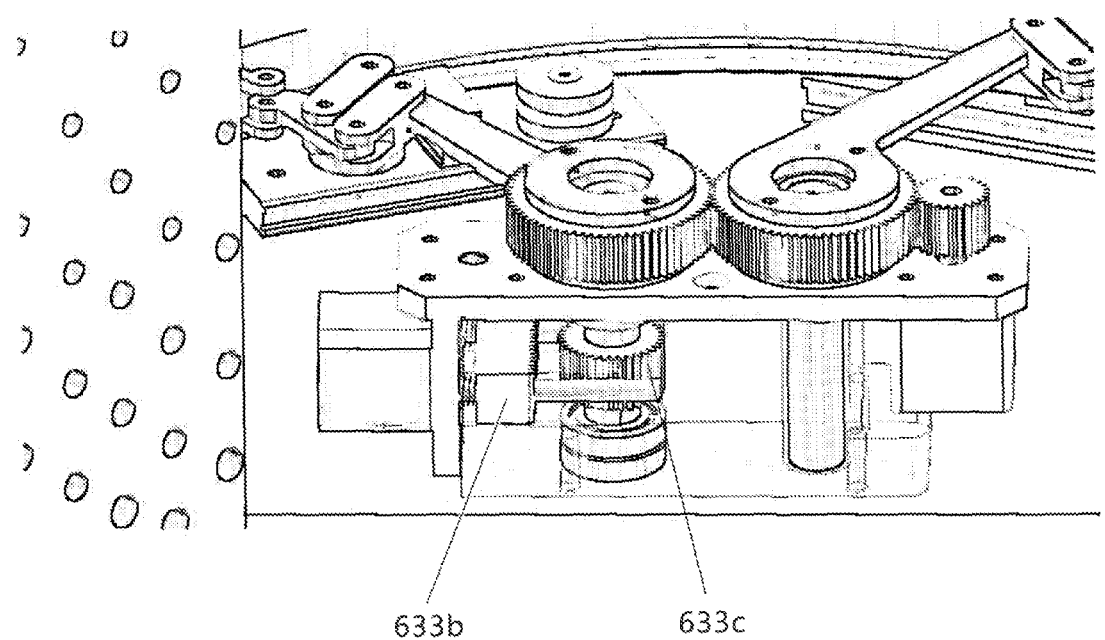
FIG. 10 is a structural schematic diagram of the driving device in an unlocked state; wherein, 1. enclosure, 2. skeleton, 3. main emission source, 4. conveying device, 5. PLC, 6. auxiliary emission source device, 11. front worktable 11a. time display, 11b. LED progress lamp, 12. back worktable, 13. top cover, 31. emission source mounting plate, 32. main emission source box, 41. conveyor belt, 41a. conveyor belt end cover, 42a. first limit rod, 42b. second limit rod, 43a. first stepping motor, 43b. third stepping motor, 44a. fixed guardrail A, 44b. movable guardrail B, 45. second stepping motor, 46. infrared induction counter, 61. rail mounting plate, 62. drawer, 63. driving device, 64. auxiliary emission source block, 631. drive gear, 632. stepping motor, 633. locking device, 634. drawer pull rod, 633a. electromagnet, 633b. rack, 633c. locking gear, 633d. fixing rod provided with a spring.

Further description of the present utility model will be made below with reference to the accompanying drawings in order to enable those skilled in the art to more clearly understand the protection scope of the present utility model.

The present utility model is efficiency enhancement field conducting equipment, which can induce the energy into the manufactured product using the independently developed efficiency enhancement field induction technology (EEFIT). The efficiency enhancement field is an energy field having a high field strength characteristic; according to the scientific test, its energy has the traits of far infrared spectrum.

As shown in the figure, an EEFIT-based electromagnetic wave energy conducting equipment, comprising an enclosure 1, a skeleton 2, main emission sources 3, conveying devices 4 and a PLC 5; the skeleton 2 is arranged in the enclosure 1, and the bottom of the skeletal structure is directly connected to stabilizers to enhance the structural strength; in order to fit different placing faces, and adjustable horizontal wheels can be used as the stabilizers; the main emission sources 3 are disposed on the emission source mounting plate 31 which is fixed on the skeleton 2; the conveying devices 4 are disposed beside the main emission sources 3 and are electrically connected to the PLC 5.

As a preferred embodiment of the present utility model, the enclosure 1 is split into two parts, upper and lower portions, and the upper portion is narrower than the lower portion. For descriptive convenience, the device is split into front and back portions according to the movement direction of the article irradiated during working, the front portion is an input end of the article irradiated, the back portion is an output end of the article irradiated; this division is just for the convenience of description and is not intended to make other definitions to the equipment of the present utility model. The front and back portions of the upper part of the enclosure 1 are provided with a front worktable 11 and a back worktable 12, respectively; the front and back ends of the conveyor belt are respectively positioned on the front and back worktables (11, 12) so that the article irradiated can be placed and taken out conveniently. The front and back panels of the upper part of the enclosure 1 are provided with a plurality of holes matched with the conveying devices 4 in position, so that the article irradiated can be input and output. For the convenience of treatment or maintenance under a special case, the top cover 13 at the upper part of the enclosure 1 is configured to be an openable structure and is provided with a lock to guarantee it is in the closed state in daily use and can be opened if required.

Each main emission source 3 essentially consists of far infrared ceramic, which can be a single piece of far infrared ceramic material or a main emission source box 32 provided with multiple small far infrared ceramic blocks therein. The far infrared ceramic is composed of the following raw materials in parts by weight: 40 parts of aplite, 20 parts of anorthite, 8 parts of jadeite, 15 parts of tephra, 1 part of talc, 5 parts of rhaetizite, 2 parts of platinum and 100 parts of industrial putty. The manufacturing method is as follows: grinding and abrading 2 kg of anorthite, 1.5 kg of tephra and 0.5 kg of rhaetizite; then burning at high temperature and then quickly cooling; and finally fixing and modeling together with 0.8 kg of jadeite, 4 kg of aplite, 0.1 kg of talc and 0.2 kg of platinum by use of 10 kg of industrial putty, so as to obtain 20 kg of far infrared ceramic.

Each conveying device 4 comprises a conveyor belt 41, a fixed guardrail A (44a), a movable guardrail B (44b) and limit rods. The conveyor belts 41 are disposed beside main emission sources 3 and can convey the articles from the front end to the back end. The fixed guardrail A (44a) is fixed at the side, near the main emission source 3, of the conveyor belt; the position of the fixed guardrail A (44a) is matched with the conveyor belt 41 to ensure that the irradiated articles get close to the main emission source 3 as much as possible and do not drop from the conveyor belt 41; the movable guardrail B (44b) is disposed at one side of the conveyor belt 41 away from the main emission source 3, and its position is matched with the conveyor belt 41, one side of the movable guardrail B (44b) is further provided with a second stepping motor 45 which is fixed on the skeleton 2 and can drive the movable guardrail B (44b) to move parallel with the fixed guardrail A (44a). The both ends of the fixed guardrail A (44a) and the movable guardrail B (44b) are narrower than that of the middle parts, the front ends of the fixed guardrail A (44a) and the movable guardrail B (44b) are near the front panel at the upper part of the enclosure, and the back ends are near the back panel at the upper part of the enclosure, thereby ensuring that the both guardrails function well as guiders for the irradiated articles so that it moves forward under the driving of the conveyor belt 41.

For the convenience of the input and output of the irradiated articles, the both ends of the conveyor belt 41 are disposed on the front worktable 11 and the back worktable 12, and the both sides of the conveyor belt 41 are provided with conveyor belt end covers 41a, thereby guiding the articles conveyed by conveyor belt 41 and preventing the articles dropping or being blocked by the shells.

Each conveyor belt 41 is provided with two limit rods, i.e. a first limit rod 42a located near the inlet side of the conveyor belt 41 and a second limit rod 42b located away from the inlet side of the conveyor belt 41. The both sides of the second stepping motor 45 are respectively provided with the first stepping motor 43a and the third stepping motor 43b; the first, the second and the third stepping motors are disposed on the same fixing profile which is fixed on the skeleton. The first and second limit rods (42a, 42b) are respectively connected with the first and the third stepping motors (43a, 43b). The first and second limit rods (42a, 42b) can move under the action of the first and the third stepping motors (43a, 43b), the first limit rod 42a can be opened or closed to allow bottles to reach the main emission source or prevent bottles from reaching the main emission source, the second limit rod 42b can be opened or closed to allow bottles to move away from the irradiation area or prevent bottles from moving away from the irradiation area. The first stepping motor 43a is at the side near the inlet of the conveyor belt 41, and the third stepping motor 43b is disposed at the side away from the inlet of the conveyor belt; also, the position of the first stepping motor 43a is away from the front end of the main emission source 3, the third stepping motor 43b is near the back end of the main emission source 3, so that bottles entering the irradiation region can be irradiated sufficiently and other articles not entering the irradiation region are not affected by the irradiation.

At most two conveying devices 4 can be deposited beside each main emission source 3, and the number of the main emission sources 3 is also optional. As one preferred embodiment of the utility model, one set of equipment contains three main emission sources 3, six conveying devices 4; wherein, each conveying device 4 can work independently and can operate according to different conditions respectively, so as to process different articles simultaneously or process similar articles according to different conditions.

In some embodiments of the utility model, the conveying device 4 further comprises an infrared induction counter 46 which is disposed right above the first stepping motor 43a and records the number of the articles passing through by sensing how many times the infrared ray is blocked by the irradiated articles. In order to get adapted to different irradiated articles, the height of the infrared induction counter 46 is adjustable, thereby ensuring all articles different in height can be sensed when they pass through.

For the convenience of checking the progress of the irradiation treatment, time displays 11a and/or LED progress lamps 11b can be further disposed on the front panel at the upper part of the enclosure 1, the time displays 11a and the LED progress lamps 11b are electrically connected to the PLC 5; the time display 11a begins to count down to calculate the remaining time after the beginning of the irradiation. The progress lamp 11b is a set of LED templates with heights from low to high; after the beginning of the irradiation, the LED progress lamp 11b can display the current treating process according to the irradiation time, the lowest portion is lightened initially, and the higher portion is lightened gradually over time, so the current radiation progress can be seen directly.

In other embodiments of the utility model, an auxiliary emission source device 6 is further arranged. The auxiliary emission source device 6 is disposed within the body at the side face of the enclosure 1 and can emit far infrared ray electromagnetic waves, such that a protective energy field can be formed for the article to be irradiated, to prevent it from the interference of energy fields of other external electromagnetic waves when it is irradiated, thus ensuring the stability of the energy conducting process. The auxiliary emission source device 6 is composed of a base, a rail mounting plate 61, drawers 62, a driving device 63 and auxiliary emission source blocks 64. The rail mounting plate 61 is fixed on the base, the drawers 62 can be movably matched with the rail mounting plate 61, and the auxiliary emission source blocks 64 are arranged in the drawers 62, the driving device 63 is used for driving the drawers 62 to move along the rail mounting plate 61. Two drawers 62 are arranged and are each shaped like a ¼ arc; the panels at two sides of each drawer 62 are matched with the opening in the side face of the machine in shape and size to ensure that the whole device looks beautiful and does not affect the opening and closing of the drawers.

The driving device 63 is composed of a fixing base, driving gears 631, a stepping motor 632, a locking device 633 and a drawer pull rods 634; there are two driving gears 631, each of which is used for driving one drawer 62 to move; the locking device 633 is used for preventing the driving gears 631 from rotating is necessary. There are two sets of drawer pull rods 634 by which the two drawers are connected to its corresponding driving gears 631 respectively, each set of drawer pull rods 634 is comprised of two drawer pull rods and a linkage, one drawer pull rod is connected with a corresponding drawer 62, the other drawer pull rod is connected to the corresponding driving gear 631, and the two drawer pull rods are connected by the linkage. The two driving gears 631 are engaged together, the stepping motor 632 is engaged with one driving gear 631 through one gear, thus driving the two driving gears 631 to rotate and realizing the movement of the drawers. The locking device 633 is comprised of an electromagnet 633a, a rack 633b, a locking gear 633c and a fixing rod 633d provided with a spring, the locking gear 633c is fixed on a fixed shaft of one driving gear 631, the rack 633b is engaged with the fixing rod 633d provided with a spring, the electromagnet 633a is disposed at the back side of the rack 633b, so that the rack 633 can be engaged with the locking gear 633c under normal condition and prevent the locking gear 633c from rotating, thereby locking the driving gears 631 and drawers 62. When the electromagnet 633a is powered up, the rack 633b moves backward, then the driving gears 631 can be rotated under the driving of the stepping motor 632, thereby opening and closing the drawers 62; the stepping motor 632 and the electromagnet 633a are electrically connected with the PLC, respectively.

The auxiliary emission source device is always in the machine; only when the auxiliary emission source blocks need to be placed, replaced or taken out, the auxiliary emission source device rotates out of the machine. When it is needed to open the drawers, the PLC sends unlock information to the locking device, then, the electromagnet is powered up, the rack moves backward, and the stepping motor 632 is energized to work to drive the driving gear to rotate, then the drawers are moved to an open position; after the opening degree is appropriate, the stepping motor 632 stops working, the electromagnet is powered down, the rack moves forward and is engaged with the locking gear to fix and strop the drawers from rotating; after the completion of the replacement, the PLC controls the stepping motor 632 to rotate reversely to drive the drawers 62 to close according to the above-mentioned steps; after the drawers are completely closed, the locking device 633 locks the drawers from moving.

The working process of the efficiency enhancement field induction based electromagnetic wave energy conducting equipment of the utility model is illustrated below with examples. Bottled water is taken as the object to be irradiated, and the area close to the main emission source on each conveyor belt is called an irradiation area. The specific working process is as follows:

1. According to the size of the bottle to be irradiated, the channel width, the rotational speed of the conveyor belt, the number of bottles to be irradiated each time, the irradiation time, the stop delay time of the conveyor belt and other parameters are set; the channel width is set through the PLC; upon the setting is completed, the PLC sends a control signal to the second stepping motor, and then the second stepping motor rotates to drive a movable guardrail B to move so as to adjust the horizontal distance between the movable guardrail B and a fixed guardrail A.

2. The conveyor belt is started, and at this time, a first limit rod retracts back, and a second limit rod stretches out; bottles to be irradiated are placed on the conveyor belt and driven forward by the conveyor belt.

3. The infrared induction counter installed at the front of the conveyor belt starts counting. When the number of bottles passing reaches a set value, the first limit rod stretches out under the action of the first stepping motor to prevent following bottles from entering the irradiation area; the conveyor belt conducts delayed working for a certain time after the first limit rod stretches out, so as to ensure that the bottles in the irradiation area are close to the main emission source to the greatest extent.

4. After the delay time is up, the conveyor belt stops working, and the irradiation timing begins; after the timing begins, the remaining time is shown on the front panel, and the LED progress lamp is on from low to high.

5. After the irradiation is completed, the first and second limit rods retract simultaneously; the conveyor belt is started to transport out the bottles that have already been irradiated and transport in the bottles to be irradiated at the same time. Meanwhile, the infrared induction counter starts counting.

6. When the quantity counted by the infrared induction counter reaches a set quantity, the first and second limit rods stretch out simultaneously, and the conveyor belt delays stopping to transport out the bottles that have already been irradiated and ensure that the bottles to be irradiated are close to the second limit rod to the greatest extent; for irradiated objects which have special requirements, such as brittle articles, the working time of the conveyor belt can be set to make it stop working immediately after it transports out irradiated objects, and the further processing can't be continued before articles are removed manually.

7. During the subsequent work, repeat Steps 5 and 6 around and around till completing the whole processing course.

8. After the irradiation of the last batch is complete, the first and second limit rods retract simultaneously; the conveyor belt rotates until all bottles are transported out, and then it can be shut down.

It's important to note that in the above embodiments and drawings, each set of equipment has three main emission sources. Two conveyor belts are set respectively on both sides of every emission source, and there are six conveyor belts in total; each conveyor belt can work independently so that different articles can be processed or different irradiation time can be set as needed.

The invention claimed is:

1. An EEFIT (Efficiency Enhancement Field Induction Technology)-based electromagnetic wave energy conducting equipment, comprising:
    an enclosure;
    a skeleton arranged within the enclosure;
    main emission sources arranged on the skeleton and configured to irradiate an article in the enclosure;
    conveying devices arranged beside the main emission sources, the conveying devices configured to transfer the article to be irradiated into and out of the enclosure; and
    a PLC (Programmable Logic Controller), the conveying devices being electrically connected with the PLC,
    wherein each conveying device comprises:
        a conveyor belt; and
        limit rods arranged on each conveyor belt, the limit rods being respectively driven by two stepping motors, which are configured to receive a control signal from the PLC.

2. The EEFIT-based electromagnetic wave energy conducting equipment of claim 1, wherein each conveying device further comprises a fixed guardrail A and a movable guardrail B; and a second stepping motor is arranged on one side of the movable guardrail B, and the second stepping motor drives the movable guardrail B.

3. The EEFIT-based electromagnetic wave energy conducting equipment of claim 1, wherein each conveying device further comprises an infrared induction counter, the infrared induction counter is electrically connected with the PLC, and the infrared induction counter is arranged right above a first stepping motor.

4. The EEFIT-based electromagnetic wave energy conducting equipment of claim 1, wherein time displays and/or LED process lamps are further arranged on the enclosure, and the time displays and the LED process lamps are electrically connected with the PLC respectively.

5. The EEFIT-based electromagnetic wave energy conducting equipment of claim 1, wherein the EEFIT-based electromagnetic wave energy conducting equipment further comprises an auxiliary emission source device, and the auxiliary emission source device is composed of a base, a rail mounting plate, drawers, a driving device and auxiliary emission source blocks.

6. The EEFIT-based electromagnetic wave energy conducting equipment of claim 3, wherein the height of each infrared induction counter is adjustable.

7. The EEFIT-based electromagnetic wave energy conducting equipment of claim 1, wherein the main emission sources are mainly composed of far infrared ceramic, and each main emission source is a single piece of far infrared ceramic material or a main emission source box provided with a plurality of small far infrared ceramic blocks therein.

8. The EEFIT-based electromagnetic wave energy conducting equipment of claim 2, wherein the widths of both ends of the fixed guardrail A and the movable guardrail B are smaller than those of the middles, and the both ends of the fixed guardrail A and the movable guardrail B are close to shells on both sides of the enclosure.

9. The EEFIT-based electromagnetic wave energy conducting equipment of claim 1, wherein the upper part of the enclosure is narrower than the lower part, and a front worktable and a back worktable are arranged on the front and back sides of the enclosure, the front worktable and the back worktable are arranged on both ends of the conveyor belts, and conveyor belt end covers are arranged on both sides of each conveyor belt.

10. The EEFIT-based electromagnetic wave energy conducting equipment of claim 1, wherein a top cover at the upper part of the enclosure is of an openable structure.

* * * * *